United States Patent [19]

Hershberger et al.

[11] 4,337,313

[45] Jun. 29, 1982

[54] IMMOBILIZATION OF BIOCATALYSTS

[75] Inventors: Donald F. Hershberger, Garfield, Ind.; Moshe M. Sternberg, Oakland, Calif.

[73] Assignee: Miles Laboratories, Inc., Elkart, Ind.

[21] Appl. No.: 214,218

[22] Filed: Dec. 8, 1980

[51] Int. Cl.³ .................... C12N 11/02; C12N 11/04
[52] U.S. Cl. .................... 435/177; 435/180; 435/181; 435/182
[58] Field of Search ............... 435/174, 177, 180, 181, 435/182

[56] References Cited

U.S. PATENT DOCUMENTS

| | | | |
|---|---|---|---|
| 3,736,231 | 5/1973 | Stanley et al. | 435/177 |
| 3,779,869 | 12/1973 | Zienty | 435/174 |
| 3,980,521 | 9/1976 | Amotz et al. | 435/174 |
| 3,989,596 | 11/1976 | Long | 435/174 |
| 4,060,456 | 11/1977 | Long | 435/174 |
| 4,090,919 | 5/1978 | Chibata et al. | 435/177 X |
| 4,212,943 | 7/1980 | Borglum | 435/180 |
| 4,224,411 | 9/1980 | Chibata et al. | 435/177 |
| 4,288,552 | 9/1981 | Gestrelius | 435/174 |

OTHER PUBLICATIONS

Ono, et al., Preparation and Properties of Immobilized Naringinase Using Tannin-Aminohexyl Cellulose, Agric. Biol. Chem. vol. 42, No. 10, 1978 (pp. 1847-1853).

Ohba et al., Immobilization of Streptomyces Flavochromogenes Pullulanase on Tannic Acid and TEA-E-Cellulose Biotechno. & Bioeng. vol. XX, 1978, (pp. 665-676).

*Primary Examiner*—David M. Naff
*Attorney, Agent, or Firm*—Jerome L. Jeffers

[57] ABSTRACT

Enzymes or enzyme producing microorganisms are immobilized by contacting an aqueous medium containing an enzyme or enzyme producing microorganism with tannin, a long chain, polyamine, cationic flocculating agent and a crosslinking agent and separating the resultant enzymatically active reaction product from the aqueous medium. The reaction product has improved physical strength for use in a column bed reactor. A preferred flocculating agent is a water soluble epihalohydrin/polyamine copolymer.

15 Claims, No Drawings

IMMOBILIZATION OF BIOCATALYSTS

BACKGROUND OF THE INVENTION

The use of enzymes derived from microbial cells to effect specific chemical transformations is well known. In carrying out such transformations, the cell-free enzyme preparation, ruptured cells or whole cells can be used as the source of biocatalyst. The free enzyme or cell can be efficiently used in batch-type processes but do not lend themselves to continuous industrial scale processes. This difficulty has led to increased interest in the preparation of various forms of immobilized enzymes.

U.S. Pat. No. 3,779,869 (issued Dec. 18, 1973) discloses the stabilization of glucose isomerase activity by treating whole bacterial cells with glutaraldehyde. The use of gluaraldehyde for the immobilization of ruptured cells to provide a coherent solid product having glucose isomerase activity is disclosed in U.S. Pat. No. 3,980,521 (issued Sept. 14, 1976).

U.S. Pat. No. 4,060,456 (issued Nov. 29, 1977) involves the stabilization of microbial cell material having glucose isomerase activity by treating it with a cationic, polyelectrolyte flocculating agent such as a polyethyleneimine or polyvinylpyrolidone. The use of polyelectrolytes such as polyamines and cationic, polyacrylamides in the stabilization of microbial cells having active enzymes associated therewith is disclosed in U.S. Pat. No. 3,989,596 (issued Nov. 2, 1976).

Ono et al describe the immobilization of naringinase from *Aspergillus niger* by adsorbing the enzyme to tanninaminohexyl cellulose prepared by the reaction of aminohexyl cellulose and cyanogen bromide activated chinese gallotannin in *Agric. Biol. Chem.*, 42(10), 1847–1853 (1978).

Ohba et al disclose in *Biotechnology and Bioengineering*, Vol. XX, Pp. 665–676 (1978) that pullulanase can be successfully immobilized by the addition of tannic acid to the culture filtrate of thermophilic *Streptomyces flavochromogenes* to form a tannin-pullulanase adduct which can then be bound to TEAE-cellulose.

There is disclosed in U.S. Pat. No. 4,212,943 (issued July 15, 1980) a bacterial cell aggregate having increased particle hardness which is produced by contacting a mass of bacterial cells with a crosslinked reaction product of glutaraldehyde or cyanuric halide and a cationic polymer obtained by polymerization of an epihalohydrin and an alkylenepolyamine.

SUMMARY OF THE INVENTION

The present invention is a method for the immobilization of an enzyme producing microorganism or the enzyme produced thereby which comprises forming a reaction product by the steps of (a) contacting an aqueous medium containing the enzyme or a mass of bacterial cells having biocatalytic activity with tannin; a long chain, polyamine, cationic flocculating agent and a crosslinking agent, and (b) separating the reaction product from the aqueous medium.

DETAILED DESCRIPTION AND PREFERRED EMBODIMENTS

The immobilization technique described and claimed herein has been found to provide a much harder reaction product than relevant prior art techniques while not affecting the biocatalytic activity of the immobilized material. The unexpected improvement in physical strength provided by the present invention alleviates problems encountered with weaker systems when used for extended periods in a column bed reactor because materials of lesser strength tend to exhibit softening or swelling which can result in flow restriction or stoppage and/or channeling.

The biocatalytic material to be immobilized by the method of this invention can be a whole fermentation harvest or filtrate or a partially purified material derived therefrom. Whole or ruptured cells as well as free enzymes may be immobilized using the present system.

Harvesting the material to be immobilized is accomplished by the use of a long chain, polyamine, cationic flocculating agent which is reacted with an excess of crosslinking agent to form a crosslinking agent/flocculating agent adduct.

Suitable flocculating agents include those polyamine, cationic materials such as poly(acrylamide), poly(ethyleneimine), poly(2-hydroxypropyl-1-N-methylammonium chloride), poly(2-hydroxypropyl-1, 1-N-dimethylammonium chloride), poly[N-(dimethylaminomethyl)-acrylamide], poly(diallyldimethylammonium chloride), poly(N,N-dimethylaminoethyl methacrylate) or poly[N-dimethylaminopropyl]-methacrylamide. A preferred flocculating agent, because of its proven compatibilty with food processing, is an epihalohydrin-polyamine copolymer commercially available under the trademark BETZ 1180 from Betz Laboratories, Inc., Trevose, Pa. BETZ 1180 has a molecular weight less than one million, contains about 0.288 millimoles of amino groups per gram of solution (based on ninhydrin assay) and is marketed as a solution containing 30 weight percent solids, based on total solution weight. This compound is disclosed in U.S. Pat. Nos. 3,915,904 and 3,953,330. The compound is described therein as a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C.

Suitable crosslinking agents include multifunctional aldehydes such as glutaraldehyde or dialdehyde starch, multifunctional organic halides such as cyanuric chloride or 1,5-difluoro-2,4-dinitrobenzene, multifunctional anhydrides such as pyromellitic anhydride or an ethylene/maleic anhydride copolymer, multifunctional azo compounds such as diazobenzidine, multifunctional isocyanates such as hexamethylenediisocyanate, multifunctional isothiocyanates such as 4,4' βdiisothiocyanatobiphenyl-2,2'-disulfonic acid and dehydrative condensation reaction agents such as ethyl chloroformate, Woodwards Reagent K, N,N'-dicyclohexylcarbodiimide or N-hydroxysuccinimide. Crosslinking can be accomplished by introducing the flocculating agent and crosslinking agent separately to the biocatalyst containing medium or, preferably, by prereaction which provides an adduct for addition to the medium.

The reactive potential of the material to be immobilized -vs- the crosslinking agent should be determined because excessive crosslinking agent may result in loss of biocatalytic activity or unnecessary expense. When a multifunctional aldehyde is used as crosslinking agent a procedure termed formol titration is used to determine reactivity with aldehyde. This procedure, which indicates the amount of readily reactable amine content of the material to be immobilized with aldehyde is as follows:

A portion of 1 dl of the material is taken in a 250 ml. beaker. From 50 to 75 ml. of water is added to thin the material for easy stirring. A magnet stirrer is added and the material adjusted to pH 8.5 using a pH meter and sodium hydroxide solution. When the pH is steady at 8.5 (allowing a couple minutes for intracellular exchange), 3.0 ml. of 37% (w/w) formaldehyde reagent grade stabilized with 10–15% (w/w) methanol is added. The pH then drops due to reaction of the free amine groups with the aldehyde.

Using a standard solution of sodium hydroxide, such as 1.0 N, the pH is brought back to 8.5 and maintained until stable for 5 minutes (about 20 to 25 minutes total time required). The amount of alkali required is the formol titration value expressed as meq/dl.

The amount of desired flocculant for the maximum aggregation of the material is determined in a preferred method of operation. A stepwise addition technique is used and maximum flocculation is verified by further additions to supernates obtained by centrifugation of the flocculated material. A pH near neutral is usually best for this determination although some variation is allowed if there are constraints due to the stability of the biocatalyst.

The material to be flocculated may be the material as is or after tannin addition and/or crosslinking agent addition. The flocculant may be a polyamine or the reaction product of the polyamine with crosslinking agent. The optimum procedure should be based on the results of the following procedure for determination of flocculant requirement to obtain maximum flocculation and separability of the desired biocatalyst from the extraneous liquid.

A portion of 500 ml. of the material to be flocculated is taken and adjusted to pH 7.0 with 2 N sodium hydroxide solution or 2 N hydrochloric acid solution. The flocculant preparation is then added gradually from a known quantity while maintaining the pH at 7. Addition is made until flocculation is achieved and the mixture is allowed to stir for about 10 minutes. Small samples are taken (two 1.7 ml. samples) and centrifuged at 10,000×g. for 5 minutes. The supernates are poured off into small test tubes.

A further small addition of flocculant is made to one of the supernates while mixing and observing carefully. If further flocculation is noticed, more flocculant is added to the main portion with stirring and pH 7 maintenance. (This addition should be 10 or 20% of the amount first added.) After 10 minutes mixing the sampling and centrifugation is repeated.

This process is continued until no further flocculation is noted upon further addition of flocculant to the supernate. When the flocculant is in excess, the other supernate sample obtained can be checked by addition of a small amount of the initial material to be flocculated or by addition of dilute tannin solution.

A good estimate of the optimum amount of flocculant to use is obtained by this procedure. If the biocatalyst is a soluble extracellular substance, then the procedure may be varied as to pH and checking of the supernates for biocatalytic activity since maximum precipitation of the biocatalyst may not coincide with maximum aggregation of the bulk of the material.

As used herein, the term tannin is intended to include either the hydrolyzable or condensed type. Suitable tannin sources are the wood and bark of the chestnut and the integument of the pecan as well as almond hulls. Quebracho is the preferred source of tannin due to economic considerations. Besides quebracho tannin, tannic acid (mol. wt. 3100–3400), gambier tannin (mol. wt. 520) and myrobalan tannins (mol. wt. 1900) are suitable.

Upon selection of the particular tannin to be used, it is desirable to determine the relative stoichiometrics of the polycationic flocculating agent with trannin in regard to their co-flocculation and reactivity with the crosslinking agent.

The polyamine flocculant reactivity with aldehyde can be determined by slight modification of the formol titration procedure previously described. In place of the 1 dl sample of flocculant a portion of 3 ml. (or g.) should be used and diluted with water to 150 to 175 ml. The balance of the procedure should be the same with the final titer expressed as meq/ml. or g. of flocculant.

The co-flocculation equivalence of tannin for the flocculant is determined by a modification of the above procedure for optimum flocculant amount determination. One ml. (or g.) or flocculant is diluted to 500 ml with water and the pH is adjusted to 7 with 2 N sodium hydroxide or 2 N hydrochloric acid solution. While maintaining the pH at 7 with stirring, the addition of a 4 g/dl solution of the tannin is made from a known quantity until precipitation occurs. After 10 minutes mixing, two 1.7 ml. samples are taken and centrifuged at 10,000×g. for 5 min. The supernates are poured off into small test tubes and further small additions of diluted flocculant or the tannin solution made while observing for precipitation to determine which material, tannin or flocculating agent, is in excess in the solution. Additions are continued until the further addition of tannin solution gives no further precipitation. The amount of tannin added can then be expressed as equivalent for co-flocculation of 1 ml. (or g.) of flocculant.

When the flocculant is employed as its reaction product with the crosslinking agent, the flocculating strength will be somewhat reduced from that of the unreacted material. The tannin equivalent can be determined directly using the reaction product in the foregoing procedure.

The use of the foregoing titrametric methods for determining the amounts of reagent would be desirable preparatory to the immobilization of commercially suitable amounts of the biocatalyst. However, when their use is not practicable, a close approximation of the optimal amounts can be obtained by using 0.5 to 1.0 g. per liter tannin, 1.0 to 1.5 g. per liter flocculating agent and 0.7 to 2.5 g. per liter of crosslinking agent for every 10 g/l of material which can be recovered from the aqueous medium by flocculation, The presently disclosed method of biocatalyst immobilization has been found to be effective regardless of whether the biocatalyst is in the form of whole cells, ruptured cells or free enzyme. Enzyme producing organisms (and the exzymes produced thereby) which can be immobilized by the technique include *Streptomyces olivaceous, S. griseus, S. olivochromogenes, S. phaeo-*

*chromogenes, Bacillus licheniformis, B. amyloliquefaciens, B. coagulans, B. awamori, B. subtilis, Aspergillus niger, A. oryzae* and *Protaminobacter rubrum.*

The method of practicing the present invention is further illustrated by the following examples:

EXAMPLE I

Biocatalyst Particles from Fermentation Filtrate (Soluble Enzyme)

A reconstituted glucoamylase filtrate was prepared by dissolving 80 g. of powdered glucoamylase preparation in 2000 ml. of water. A portion, 1900 ml., of the resultant solution was flocculated with 11 ml. of a 5 g/dl solution of poly (ethyleneimine) in water at a pH adjusted to 7 by use of acetic acid. This amount of poly (ethyleneimine) (PEI) was 20% in excess of the amount determined necessary for flocculation.

To the flocculated slurry was added 9.6 ml. of a 4 g/dl solution of tannic acid (NF grade) in water. This is the amount of tannic acid which was found to be equivalent for flocculation of the excess of PEI employed.

Glutaraldehyde (3 meq) was added as a dilution of 0.6 ml. of 25% (w/w) glutaraldehyde solution in about 100 ml. of water. This amount was based on the stoichiometric requirement determined by formol titration.

The final pH was adjusted from 6.5 to 7.5 using a 1 N sodium hydroxide solution and, after standing for 1 hour at room temperature, the aggregated solids were recovered by centrifugation at about $10,000 \times g$. for 15 minutes. The damp solids were then extruded and the noddle shaped particles were dried in a vacuum oven with a slight bleed-in of air at 50° C. for 16 hours. The resulting dried extrudate was broken up into particles. The particles were found to contain the desired biocatalytic (glucoamylase) activity when placed in a solution of 1 g/dl maltose in 0.1 M sodium acetate buffer of pH 4.2 at 50° C. The biocatalytic activity was determined by an increase in the concentration of glucose in the substrate as determined by checking with DEXTROS-TIX ® Reagent Strips. The glucsoe concentration increased from approximately 0 mg/dl to 20 mg/dl in 2 minutes at room temperature in a mixture of 50 ml. substrate with 200 mg. of the biocatalyst. The mixture was then incubated with agitation at 50° C. After 40 minutes the glucose concentration was >250 mg/dl.

The particles were filtered, washed and transferred to a fresh portion of the above described substrate where they again exhibited the desired biocatalytic activity in which the glucose concentration increased to >250 mg/dl in 40 minutes. An incubated control substrate indicated about 0 mg/dl in 40 minutes. On continued soaking in the substrate, the particles maintained their physical integrity without significant softening.

EXAMPLE II

Biocatalyst Particles from Whole Fermentation Harvest

In this example, portions of a fermentation with a mutant strain of *Streptomyces olivaceous* containing intracellular glucose isomerase were employed. The dry weight of cell content was 7.5 g./l. A formol titer of the reaction of formaldehyde at pH 8.5 was determined to be 7.4 meq/l.

The following additions were made to a 1 liter portion of the fermentation: A total of 1.0 g. quebracho extract tannin was added after predissolving in water at 4 g./dl concentration. This was done at the initial pH 5.15 of the harvest. The pH was then adjusted to 9.0 with 2 N sodium hydroxide.

A preparation of an epihalohydrin/polyamine copolymer (BETZ 1180 from Betz Laboratories, Inc.) hereinafter referred to as polyamine flocculating agent was mixed with glutaraldehyde by adding the polyamine to an aqueous glutaraldehyde solution of about 3.5% (w/w) concentration. The polyamine had been prediluted in water to about 2% solids and the pH adjusted to 9.0 which was maintained during the addition of the amine. The final mixture was comprised of 1.77 g./dl glutaraldehyde and 1.3 g./dl polyamine which provided an excess of aldehyde of 0.34 meq/ml. The mixture of glutaraldehyde and polyamine was added to the pH 9 adjusted fermentation harvest containing tannin at a level of 112.5 ml./L initial harvest volume. This was found to be the usual requirement for flocculation of such fermentations. The final glutaraldehyde conentration was in excess of the stoichiometric requirement by 30 meq/l.

After addition of the polyamine/glutaraldehyde adduct, the pH was again adjusted to 9. The mixture was aged for about 3 hours and the aggregated solids filtered by vacuum and retained on paper discs. The cake obtained was removed from the paper and extruded by hand using a 10 cc plastic syringe having an orifice of 1.5 mm diameter. The extrudate was dried for a few hours under a hood with moderate air flow and then in a forced air oven at 60° C. for 8 hours.

Other preparations were made for comparison in which one of the reagents was omitted or only the tannin or glutaraldehyde was used for recovery of the aggregate. In these instances, the aggregates formed were often not recoverable easily by filtration and so were centrifuged and dehydrated to comparable filter cake moisture by pressing between layers of paper. Other conditions of recovery remained the same. When either the polyamine or glutaraldehyde were omitted, the adduct was not prepared, but the reagents were utilized at the same dilutions as the adduct preparation. Tannin by itself was also evaluated at pH 7 which gave better flocculation than at pH 9.

The dried materials prepared as described above were grounded gently by hand with mortar and pestle and the ground material passing through a No. 24 mesh Tyler equivalent screen and collecting on a No. 28 mesh Tyler equivalent screen was retained. The material was evaluated for strength after rehydration in a compression cell and the relative strength determined from the work necessary to compress the sample to a fractional volume of the original rehydrated volume.

The hardness is expressed in relation to resistance to compression of the bacterial cell aggregate particles. An Instron Universal Tester Model 1102 was employed in a manner similar to that described in U.S. Pat. No. 3,935,069. This instrument is available from Instron Corporation, Canton, Mass.

The load or test cell employed with the above Instron Tester consists of a transparent acrylic plastic cylinder having an I.D. of 1.720 in. (4.37 cm.), an O.D. of 2.520 in. (6.54 cm.) and a height of 8.5625 in. (21.8 cm.). The bottom portion has a step 0.25 in. (0.635 cm.) thick with an opening of 1.5 in. (3.81 cm.) to form a support for a micro-filter. A convenient micro-filter is a spinnerette employed in textile spinning having 14,500 openings about 0.008 in. (0.2032 mm.) diameter.

A Type 304 stainless steel plunger 1.693 in. (4.3 cm.) diameter and 5.375 in. (13.66 cm.) long is mounted so as to move coaxially into the above cylinder. Appropriate indicia are located along the load cell to show a sample depth of 4 in. (10.17 cm.). Provisions are also made for applying a reduced pressure or vacuum to the bottom of the load cell and for collecting any liquid which passes through the micro-filter.

If a sample of bacterial cell aggregate is placed in the above load cell and pressure is applied to the sample through the plunger, the sample will be compressed. The pressure needed to compress the sample a given amount is an indication of the sample hardness.

The results of this experiment are set out in Table I:

TABLE I

| Sample | Relative Strength |
|---|---|
| The described treatment | = 100 |
| Tannin omitted | 68 |
| Glutaraldehyde omitted | 49 |
| Polyamine omitted | nil* |
| Glutaraldehyde only | nil* |
| Tannin only (pH 9) | nil* |
| Tannin only (pH 7) | nil* |

*These samples lost integrity of their particles when rehydrated and had inadequate strength to properly test.

All of the above particles exhibited the desired biocatalytic (glucose isomerase) activity.

EXAMPLE III

Biocatalyst Particles from Fermentation Harvest

In this example of the recovery of a fermentation harvest from a mutant strain of Streptomyces olivaceus, the glutaraldehyde excess was reduced from 30 meq/l. to 4 meq/l. in the final mixture.

The method employed was addition of only part of the polyamine/glutaraldehyde adduct followed by more polyamine (of same dilution) to give flocculaton.

Tannic acid additions of 0.5 g. and 1.0 g. per liter of initial harvest were made using a 4 g./dl aqueous solution. Other conditions of the recovery were as in the previous example. The resulting strengths of the rehydrated particles are set out in Table II.

TABLE II

| Sample | Relative Strength |
|---|---|
| Tannic acid omitted | = 100 |
| 1 g./l. tannic acid concentration | 110 |
| 0.5 g./l. tannic acid concentration | 111 |
| Tannic acid omitted, 30 meq/l. aldehyde excess | 94 |

The 1 g./l. level of tannic acid was equivalent for coflocculation of 27% of the polyamine/glutaraldehyde adduct (13.5% for the 0.5 g./l. level).

All of the particles exhibited the desired biocatalytic (glucose isomerase) activity.

EXAMPLE IV

Biocatalyst Particles from Fermentation Harvest

A fermentation harvest of a mutant strain of Streptomyces olivaceus was the starting material in this experiment. It had a dry cell content of 7.35 g./l., a pH of 7.3 and an aldehyde reactive capacity of 44.7 meq/l. at pH 8.5.

A 227 liter portion of the fermentation harvest was treated with 2.5 N sodium hydroxide to give a pH of 9.0. Twenty-five liters of a polyamine/glutaraldehyde adduct prepared as in Example II was then added gradually with mixing. The final pH was 8.8. After one hour of gentle agitation, the aggregated solids were recovered by filtration. The solids cake was then extruded, dried in forced air at 60° C. and milled into coarse particles.

In a similar manner, to 257 liters of the harvest was added 257 g. of quebracho tannin extract as a 3.9 g./dl. solution in water. One hour after mixing in, the pH was adjusted from 7.2 to 9.0 with 2.5 N sodium hydroxide. Thereafter, 28.3 liters of the polyamine/glutaraldehyde adduct was added gradually with mixing.

After recovery, as in the first portion without tannin, similar sized particles were evaluated for mechanical strength after rehydration. The sample without tannin was assigned a relative strength of 100 whereas the sample with tannin was found to have a relative strength of 190.

These particles exhibited the desired biocatalytic (glucose isomerase) activity.

EXAMPLE V

Biocatalyst Particles from Fermentation Harvest

Another fermentation of the type described in Example IV was used in which the dry cell content was 6.26 g./l. and the pH was 5.3. The content of aldehyde reactive material at pH 8.5 was 32.1 meq/l. Using a similar procedure as in the previous example, the amounts of reagents were as follows:

| Portion 1: | 200 liters harvest |
| | 18.8 liters polyamine/glutaraldehyde |
| Portion 2: | 189 liters harvest |
| | 189 g. quebracho tannin extract |
| | 17.7 liters polyamine/glutaraldehyde |

Portions of each batch having the same particle size were evaluated for strength after rehydration.

| Sample | Relative Strength |
|---|---|
| Without tannin | = 100 |
| With tannin addition | 224 |

The particles exhibited the desired biocatalytic (glucose isomerase) activity.

EXAMPLE VI

Biocatalyst Particles from Fermentation Harvest

A fermentation harvest of a mutant strain of Bacillus licheniformis ATCC 31604 was decanted to separate it from some noncellular dense solids. The aldehyde reactive content, determined by formol titration at pH 8.5, was 91.3 meq/l.

A 500 ml. portion was taken and adjusted to pH 8. Next was added 150 ml. of a polyamine/epihalohydrin and glutaraldehyde adduct as prepared in Example II. This amount was somewhat in excess of that required for best flocculation. Quebracho tannin extract was then added as 10 ml. of a 4 g./dl solution. After standing one hour, the aggregated solids were recovered by centrifugation and then extruded using a plastic syringe and dried at 60° C. in a forced air oven.

Particles were obtained by gentle grinding of the dried material. When these particles were rehydrated in a 40% w/w glucose solution they retained their physical integrity and biocatalytic (glucose isomerase) activity after continued soaking at 70° C. for 24 hours.

EXAMPLE VII

Immobilization of Biomass Containing Palatinose Forming Enzyme Activity

Small scale fermentation studies were carried out in two 14 liter Chemapec LF-14 fermenters (working volume 10 liters). Each fermenter was equipped with dissolved oxygen and pH measurement and was periodically coupled via tubing to a Perkin-Elmer MGA-1200 process gas analyzer for the measurement of $CO_2$, argon, oxygen, nitrogen, $H_2O$ and $NH_3$ in the off-gas from the fermentation; $CO_2$, of course, was of primary interest.

The fermentation medium consisted of beet thick juice at a concentration of 5 Brix supplemented with 0.1% $(NH_4)_2HPO_4$ and 2.0% corn steep liquor.

The fermentation vessel was inoculated with 100 ml. of a *Protaminobacter rubrum* inoculum obtained by growing a stock culture in the medium described above which was then incubated at 30° C. while being rotated at 290 RPM on a rotary shaker for 24 hours before the inoculation. After approximately 15 hours, the biomass used in the subsequent stabilization experiment was recovered from the fermentation vessel.

An immobilization procedure (Method 2) within the scope of the present invention and four methods not within the scope of the present invention, were carried out on the fermentation broth described above whose formol titration value was 0.61 meq/l.

Immobilization Methods

Method 1

Five hundreds (500) ml. of whole broth was adjusted to pH 6.5 from 4.95 with 1.0 N NaOH. To this was added 55 ml. of glutaraldehyde/polyamine adduct prepared as follows:

1. 11.67 g. BETZ 1180 diluted to 100 ml. in $H_2O$;
2. Adjust pH to 9.0;
3. 17.8 ml. of 25% glutaraldehyde diluted to 100 ml. in $H_2O$;
4. Add BETZ 1180 solution to glutaraldehyde slowly;
5. Readjust pH to 9.0;

and the combination allowed to react at 25° C. for one hour.

Method 2

To 500 ml. of whole broth was slowly added 12.5 ml. of a 4.0 g./dl solution of quebracho tannin until flocculation of the cells occurred. The solution was maintained at 25° C. for 30 minutes at which point the pH of the solution was adjusted to 6.5 with 1.0 N NaOH and 65 ml. of the glutaraldehyde/polyamine solution prepared as described in Method 1 was added. The solution was then maintained at 25° C. for one hour.

Method 3

To 500 ml. of whole broth was added 12.5 ml. of 4.0% w/v quebracho tannin. After adjusting the pH to 6.5 with 1.0 N NaOH, 60 ml. of 1.67% glutaraldehyde was added and the solution maintained at 25° C.

Method 4

To 500 ml. of whole broth was added 2.5 ml. of 10% w/v polyethyleneimine (PEI). This was maintained at 25° C. for 30 minutes. The pH of this solution was adjusted to 6.5 with 1.0 N NaOH and 50 ml. of 1.67% w/v glutaraldehyde was added. The resultant was maintained at 25° C. for one hour.

Method 5

Five hundred (500) ml. of whole broth was titrated to pH 5 with a solution of 10% PEI. The solution was maintained at 25° C. for 30 minutes whereupon 50 ml. of 1.67% w/v glutaraldehyde was added.

In all of the above methods the flocculated cells were allowed to settle and the supernatant was decanted. The remainder of the slurry was centrifuged at 10,000 RPM for 10 minutes at 25° C. in a Sorvall RC-2B centrifuge using a type GSA head. The fixed, precipitated biomass was then extruded through a standard 100 ml. hypodermic syringe by forcing by hand pressure the paste through the syringe opening (1.1–1.5 mm.) with no needle attached. The noodle-like extrudate was dried at 40° C. in a forced air drying oven and broken up into appropriately sized particles for further testing. The results of such tests are set out in Table III.

TABLE III

| Method | Dry Wt. (g.) Obtained | Instron[1] Work Value kg/in. | Character of Extrudate | Assay[2] μ mol/g. | %[3] Activity |
|---|---|---|---|---|---|
| 1 | 3.09 | 0.20 | Weak | 3,728 | 23.0 |
| 2 | 3.71 | 0.26 | Strong (best) | 3,456 | 25.6 |
| 3 | 2.07 | — | Mushy-Weak | 594 | 2.5 |
| 4 | 3.18 | — | Weak | 1,054 | 6.7 |
| 5 | 3.78 | — | Strong | 1,122 | 8.5 |

[1] The strength of the granule was determined using an Instron Universal Tester. The extrudate from Method 5 appeared to be relatively strong but was not tested because of its low activity.
[2] Immobilized enzyme assay 5 mg. of the immobilized enzyme, particle size $<80\sim>$ 150 mesh was suspended in 1 ml. of 0.01 M $PO_4$ buffer at pH 7.0 and kept at room temperature for 60 min. The hydrated enzyme was then transferred to 100 ml. of a 10% sucrose solution in the buffer and incubated at 30° C. for 60 min. while shaking. The reaction was stopped by placing the sample in a boiling water bath for 5 min. and the DNS reducing sugar assay method was employed.
[3] Activity in the broth was 100 μMol/ml.

What is claimed is:

1. A method for the immobilization of an enzyme producing microorganism or the enzyme produced thereby which comprises forming a reaction product by the steps of:
   (a) contacting an aqueous medium containing the enzyme or a mass of bacterial cells having biocatalytic activity with tannin; a long chain, polyamine, cationic flocculating agent selected from the group consisting of poly(acrylamide), poly(ethyleneimine), poly(2-hydroxypropyl-1-N-methylammonium chloride), poly(2-hydroxypropyl-1,1-N-dimethylammonium chloride), poly[N-(dimethylaminomethyl)-acrylamide], poly(diallyldimethylammonium chloride), poly(N,N-dimethylaminoethyl methacrylate), poly[N-dimethylaminopropyl]-methacrylamide and a water soluble epihalohydrin/polyamine copolymer and a crosslinking agent selected from the group consisting of a multifunctional aldehyde, a multifunctional organic halide, a multifunctional anhydride, a multifunctional azo compound, a multifunctional isocyanate and a multifunctional isothiocyanate, and
   (b) separating the reaction product from the aqueous medium.

2. The method of claim 1 wherein the immobilized material is a free enzyme.

3. The method of claim 1 wherein the immobilized material is in the form of a whole or ruptured microorganism cell.

4. The method of claim 1 wherein the flocculating agent is water soluble epihalohydrin/polyamine copolymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each lower alkyl of from 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C.

5. The method of claim 1 wherein the crosslinking agent is glutaraldehyde.

6. The method of claim 1 wherein quebracho tannin is employed.

7. The method of claim 1 wherein tannic acid is employed.

8. The method of claim 1 wherein the cationic flocculating agent and crosslinking agent are prereacted to form an adduct before their contacting with the biocatalyst.

9. The method of claim 1 wherein the enzyme producing microorganism is *Streptomyces olivaceous, S. griseus, S. olivochromogenes, S. phaeochromogenes, Bacillus licheniformis, B. amyloliquefaciens, B. coagulans, B. awamori, B. subtilis, Aspergillus niger, A. oryzae* or *Protaminobacter rubrum*.

10. A method for the immobilization of *Streptomyces olivaceous* which comprises the consecutive steps of:
 (a) providing an aqueous medium containing whole cells of the microorganism;
 (b) adding quebracho tannin to the aqueous medium;
 (c) adding an adduct of glutaraldehyde and an epihalohydrin/polyamine copolymer to the aqueous medium to form a reaction product;
 (d) removing the reaction product from the aqueous medium; and
 (e) drying the reaction product at an elevated temperature.

11. A method for the immobilization of *Bacillus licheniformis* which comprises the consecutive steps of:
 (a) providing an aqueous medium containing the microorganism cells;
 (b) adding glutaraldehyde and an epihalohydrin/polyamine copolymer to the aqueous medium;
 (c) adding quebracho tannin to the aqueous medium to form a reaction product;
 (d) removing the reaction product from the aqueous medium; and
 (e) drying the reaction product at an elevated temperature.

12. A method for the immobilization of *Protaminobacter rubrum* which comprises the steps of:
 (a) providing an aqueous medium containing the microorganism cells;
 (b) adding tannin to the aqueous medium;
 (c) adding an adduct of glutaraldehyde and an epihalohydrin/polyamine copolymer to the aqueous medium to form a reaction product;
 (d) removing the reaction product from the aqueous medium; and
 (e) drying the reaction product.

13. The method of claim 12 wherein the reaction product is contacted with sucrose to thereby convert it to palatinose.

14. The method of claim 12 wherein the tannin is quebracho tannin and it is added to the aqueous medium before the adduct.

15. An immobilized enzyme or enzyme producing microorganism produced by the method of claim 1.

* * * * *